(12) United States Patent
Griesbach, III et al.

(10) Patent No.: US 6,868,984 B2
(45) Date of Patent: Mar. 22, 2005

(54) METHOD OF DISPENSING A FACE MASK

(75) Inventors: Henry L. Griesbach, III, Clarkston, GA (US); Linda G. Harris, Lawrenceville, GA (US); David Craige Strack, Canton, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/253,062

(22) Filed: Sep. 24, 2002

(65) Prior Publication Data

US 2004/0056043 A1 Mar. 25, 2004

(51) Int. Cl.[7] .................................................. B65H 1/00
(52) U.S. Cl. .......................... 221/63; 221/303; 221/307
(58) Field of Search .................................. 221/303, 307, 221/63

(56) References Cited

U.S. PATENT DOCUMENTS

| | | | |
|---|---|---|---|
| 2,112,960 A | * | 4/1938 | Harvey ........................ 221/46 |
| 2,290,885 A | | 7/1942 | Lehmberg |
| 2,378,929 A | | 6/1945 | Joyce |
| 2,921,581 A | | 1/1960 | Swearingen et al. |
| 3,038,470 A | | 6/1962 | Campbell |
| 3,220,409 A | | 11/1965 | Liloia et al. |
| 3,308,816 A | | 3/1967 | Franklin et al. |
| 3,338,992 A | * | 8/1967 | Kinney |
| 3,341,394 A | * | 9/1967 | Kinney |
| 3,502,763 A | * | 3/1970 | Hartman |
| 3,542,615 A | * | 11/1970 | Dobo et al. |
| 3,602,913 A | | 9/1971 | Neese |
| 3,692,618 A | * | 9/1972 | Dorschner et al. |
| 3,768,100 A | | 10/1973 | Colman et al. |
| 3,802,817 A | * | 4/1974 | Matsuki et al. |
| 3,849,241 A | * | 11/1974 | Butin et al. |
| 3,881,632 A | | 5/1975 | Early et al. |
| 3,953,566 A | * | 4/1976 | Gore |
| 4,014,616 A | * | 3/1977 | Mast et al. ................... 401/292 |
| 4,041,203 A | * | 8/1977 | Brock et al. |
| 4,187,390 A | * | 2/1980 | Gore |
| 4,215,682 A | | 8/1980 | Kubik et al. |
| 4,269,315 A | | 5/1981 | Boyce |
| 4,296,746 A | | 10/1981 | Mason, Jr. et al. |
| 4,340,563 A | | 7/1982 | Appel et al. |
| 4,354,489 A | | 10/1982 | Riaboy |

(List continued on next page.)

FOREIGN PATENT DOCUMENTS

| | | |
|---|---|---|
| EP | 758009 | 3/1999 |
| WO | WO 89/01902 | 3/1989 |
| WO | 98/54991 | 12/1998 |
| WO | 99/61089 | 12/1999 |
| WO | 00/69497 | 11/2000 |
| WO | 02/49467 | 6/2002 |

OTHER PUBLICATIONS

*American Society for Testing and Materials*, ASTM Designation: D 2979–88, "Standard Test Method for Pressure–Sensitive Tack of Adhesives Using an Inverted Probe Machine", Oct. 1988, pp. 194–196.

*Primary Examiner*—David H. Bollinger
(74) *Attorney, Agent, or Firm*—Dana E. Stano; Scott B. Garrison

(57) ABSTRACT

A stack of face masks is disclosed. The stack is formed from a plurality of shaped face masks having an inside surface and an outside surface. The inside surface includes a periphery with an adhesive material disposed on at least a portion thereof. The masks are positioned in a nestled relation to one another, the inside surface of the mask being apposed to the outside surface of an adjacent mask, thereby forming a stack. The masks are adapted to maintain a distance between apposed masks so that the periphery of a mask does not contact the outside surface of an apposed mask.

22 Claims, 7 Drawing Sheets

U.S. PATENT DOCUMENTS

| | | |
|---|---|---|
| 4,374,888 A | 2/1983 | Bornslaeger |
| 4,375,718 A | 3/1983 | Wadsworth et al. |
| 4,454,881 A | 6/1984 | Huber et al. |
| 4,467,799 A | 8/1984 | Steinberg |
| 4,550,856 A | 11/1985 | Ballmann et al. |
| 4,592,815 A | 6/1986 | Nakao |
| 4,643,182 A | 2/1987 | Klein |
| 4,688,566 A | 8/1987 | Boyce |
| 4,726,365 A | 2/1988 | Jablonski |
| 4,807,619 A | 2/1989 | Dyrud et al. |
| 4,817,636 A | 4/1989 | Woods |
| 4,856,535 A | 8/1989 | Forbes |
| 4,873,972 A | 10/1989 | Magidson et al. |
| 4,874,659 A | 10/1989 | Ando et al. |
| 4,951,664 A | 8/1990 | Niemeyer |
| 4,969,473 A | 11/1990 | Bothwell |
| 5,012,952 A | 5/1991 | Franz |
| 5,014,878 A | 5/1991 | Janz |
| 5,033,115 A | 7/1991 | Bowling et al. |
| 5,067,633 A | 11/1991 | Grosz et al. |
| 5,145,727 A | 9/1992 | Potts et al. |
| 5,156,911 A | 10/1992 | Stewart |
| 5,169,706 A | 12/1992 | Collier, IV et al. |
| 5,178,931 A | 1/1993 | Perkins et al. |
| 5,188,885 A | 2/1993 | Timmons et al. |
| 5,201,869 A | 4/1993 | Roethel |
| 5,237,986 A | 8/1993 | Seppala et al. |
| 5,374,458 A | 12/1994 | Burgio |
| 5,387,450 A | 2/1995 | Stewart |
| 5,401,446 A | 3/1995 | Tsai et al. |
| 5,414,867 A | 5/1995 | Bowling et al. |
| 5,419,318 A | 5/1995 | Tayebi |
| 5,538,013 A | 7/1996 | Brannon |
| 5,561,863 A | 10/1996 | Carlson, II |
| 5,618,281 A | 4/1997 | Betrabet et al. |
| 5,640,974 A | 6/1997 | Miller |
| 5,658,270 A | 8/1997 | Lichstein |
| 5,682,879 A | 11/1997 | Bowers |
| 5,690,121 A | 11/1997 | Miller |
| 5,724,964 A | 3/1998 | Brunson et al. |
| 5,753,343 A | 5/1998 | Braun et al. |
| 5,803,077 A | 9/1998 | Gazzara |
| 5,819,731 A | 10/1998 | Dyrud et al. |
| 5,865,196 A | 2/1999 | Foote |
| 5,883,026 A | 3/1999 | Reader et al. |
| 5,918,598 A | 7/1999 | Belfer et al. |
| 5,934,275 A | 8/1999 | Gazzara |
| 5,954,055 A | 9/1999 | Miyake |
| 6,055,982 A | 5/2000 | Brunson et al. |
| 6,070,580 A | 6/2000 | McDonald et al. |
| 6,095,143 A | 8/2000 | Dyrud et al. |
| 6,098,201 A | 8/2000 | Boros, Sr. |
| 6,102,040 A | 8/2000 | Tayebi et al. |
| 6,135,988 A | 10/2000 | Turner et al. |
| 6,148,817 A | 11/2000 | Bryant et al. |
| 6,196,223 B1 | 3/2001 | Belfer et al. |
| 6,308,330 B1 | 10/2001 | Hollander et al. |
| 6,394,090 B1 | 5/2002 | Chen et al. |
| 6,401,716 B1 | 6/2002 | Sword et al. |

\* cited by examiner

METHOD OF DISPENSING A FACE MASK

BACKGROUND OF THE INVENTION

Disposable face masks have been manufactured for many years. In the medical field, early masks were designed to protect patients from pathogens contained in the exhaled air of health care personnel. In recent years, it has likewise become important to protect the health care personnel from airborne pathogens emitted by patients.

During surgical procedures, health care personnel are often required to enter and exit sterile environments to obtain equipment, supplies, and the like. Upon entry into an examination or surgical area, the health care worker dons a face mask for protection of himself and of the patient. However, face masks that are currently available require use of both hands to be properly donned. As a result, the worker may have to either place the supplies or equipment on a surface to properly don the mask, or he may have to simply hold the mask in position while transporting the supplies.

There is currently a need for a face mask that is easy to don so that proper mask usage is encouraged. More particularly, a need exists for a face mask that may be donned with a single hand so the sterility of the examination or surgical environment is not compromised.

SUMMARY OF THE INVENTION

The present invention is directed to a method of dispensing a mask and a dispenser for dispensing a mask. It is further directed to a stack of face masks that may be used with the method and/or dispenser of the present invention.

The present invention relates to a method of dispensing a face mask including providing a shaped face mask having an inside surface and an outside surface, where the outside surface is adapted to be gripped with a single hand. The mask is positioned in a nestled relation to another mask, the inside surface of the mask apposed to the outside surface of the other mask, thereby forming a stack having an outermost mask. A dispenser is provided for storage of the stack and dispensing of the outermost mask. The dispenser includes a plurality of walls and a dispensing end, and the dispensing end including a resilient diaphragm having an opening. The stack is placed in the dispenser such that at least a portion of the outermost mask may be gripped through the opening. The outermost mask may then be removed through the opening, the resilient diaphragm retaining the remainder of the stack in the housing, so that the mask apposed to the dispensed mask becomes the outermost mask.

The present invention further relates to an apparatus for dispensing a mask from a stack of a plurality of shaped masks. The dispensing system includes a dispenser having a stack of a plurality of shaped masks contained therein, and an opening toward which the stack is biased. The dispenser further includes a flexible support element disposed astride the opening adapted to secure the stack from dislodgment while being sufficiently yieldable to allow the mask to overcome the flexible support element and be removed from the dispenser. In some embodiments, the mask may include an outside surface adapted to be gripped through the opening.

The present invention further relates to a stack of face masks including a plurality of shaped face masks having an inside surface and an outside surface, the inside surface having a periphery with an adhesive material disposed on at least a portion thereof. The masks are positioned in a nestled relation to one another, the inside surface of the mask being apposed to the outside surface of an adjacent mask, thereby forming a stack. The masks are adapted to maintain a distance between apposed masks so that the periphery of a mask does not contact the outside surface of an apposed mask. In some embodiments, the shape of the mask is adapted to maintain the distance between apposed masks. In other embodiments, the outside surface is adapted to maintain the distance between apposed masks. A distance of at least 3 millimeters is generally maintained.

DESCRIPTION OF THE INVENTION

The present invention relates to a face mask that is designed to be gripped with a single hand and a stack of such face masks. It further relates to a dispenser for such masks.

Figure 1:
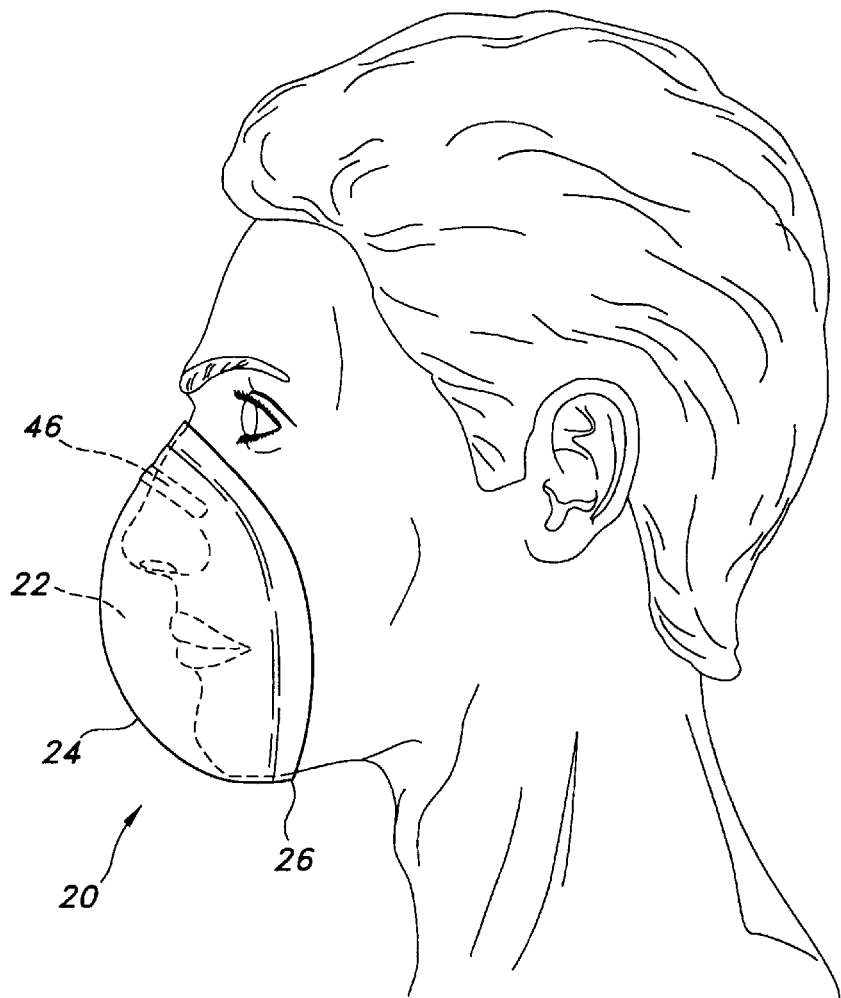
FIG. 1 is a side plan view of an exemplary cup shaped face mask donned by a wearer.

One embodiment of a face mask 20 is illustrated in FIG. 1. However, it should be understood that other embodiments are encompassed by the present invention. The face mask 20 is generally sized to fit over the nose and mouth of a wearer, and includes an inside surface 22, i.e., the surface proximal to the face of the wearer, and an outside surface 24, i.e., the surface distal to the face of the wearer. The inside surface 22 includes a periphery 26 that is adapted to engage the face of the wearer when the mask is donned. The periphery 26 is generally a flange, and may be folded as in FIGS. 3 and 4, flared as in FIGS. 5–8, or any other configuration (not shown), provided that the contact area with the face of the wearer is sufficient.

Figure 2:
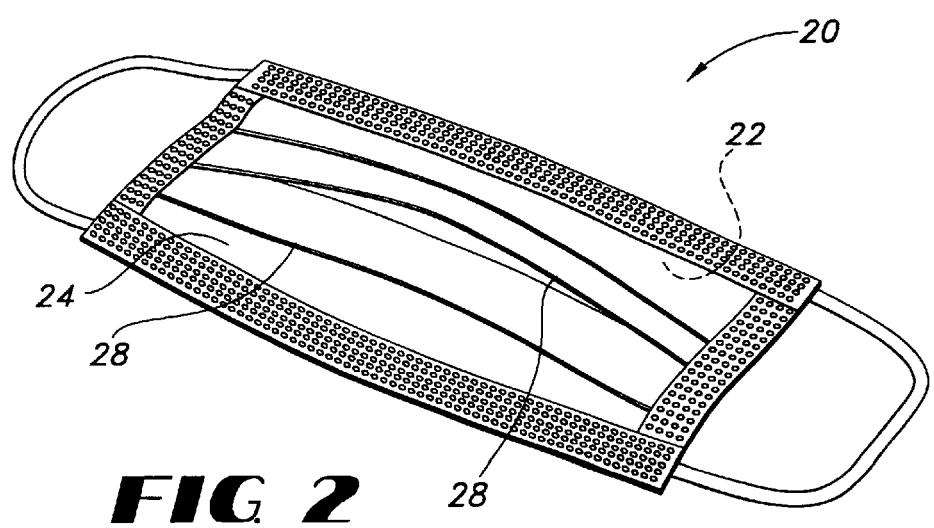
FIG. 2 is a perspective view of a rectangular pleated face mask in a partially open configuration.

The present invention relates to any style or configuration of shaped face mask that is sufficiently rigid so that the mask may be gripped with a single hand without crushing or collapsing. As used herein, the term "shaped" means having a resilient structure that is able to retain its form and dimension. Thus, a shaped face mask may be dispensed and donned without crushing or collapsing. While sufficient rigidity is required for handling, the mask must also be somewhat flexible so that the periphery of the mask is able to substantially conform to the contours of the wearer's face. In some embodiments, the mask may be cup shaped as in FIGS. 1, 3, and 5–14. In other embodiments, the mask may be cone shaped (not shown). Alternatively, the mask 20 may have a rectangular shape (FIG. 2) with pleats 28, provided that the mask 20 is packaged (not shown) in at least a partially opened or expanded configuration (FIG. 2) so that the wearer can grasp the mask 20 with a hand and apply it directly to the face without having to manually expand the pleats 28. Various techniques may be used to increase the rigidity of the mask. In some embodiments, the mask may be thermally molded or heat set to increase stiffness. In other embodiments, binder chemicals may be added to the materials prior to formation of the mask.

Figure 3:
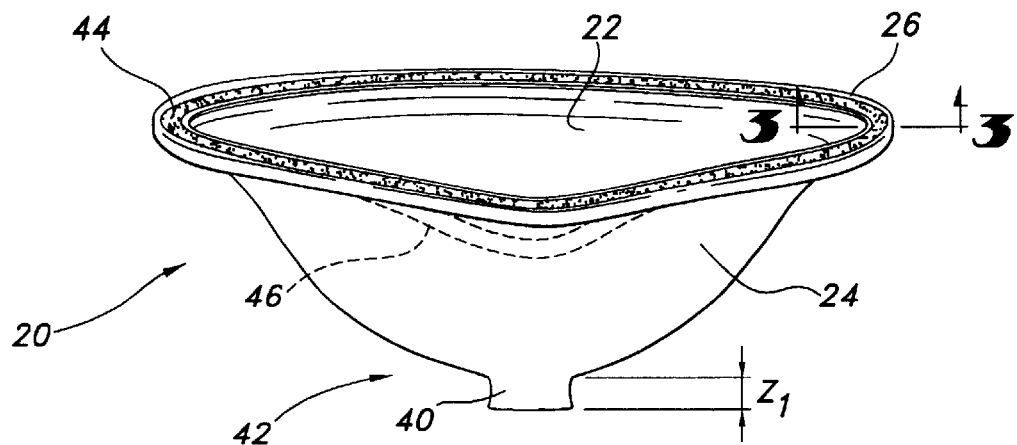
FIG. 3 is a perspective view of a cup shaped face mask having a folded edge periphery and an integral tab positioned so that the mask can be gripped with a single hand.
Figure 4:
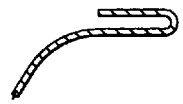
FIG. 4 is a broken-away side plan view of the folded edge periphery of the mask depicted in FIG. 3 taken along a line 3—3.
Figure 5:
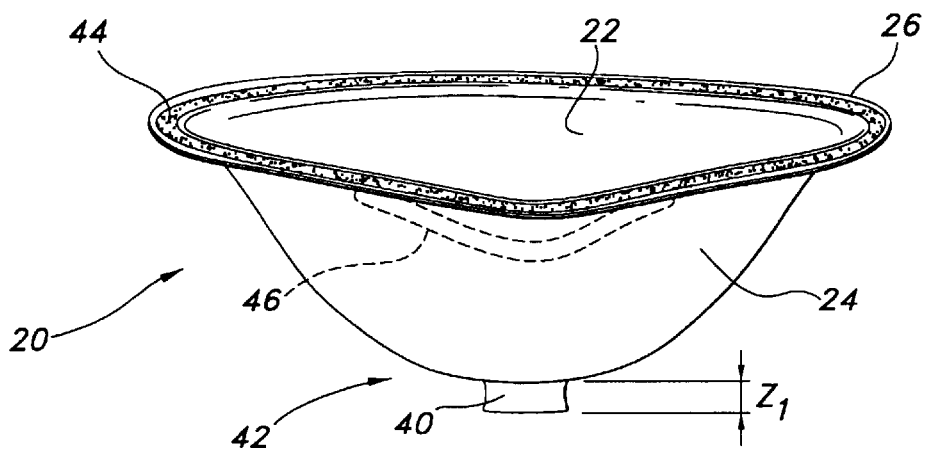
FIG. 5 is a perspective view of a cup shaped face mask having a flared edge periphery and an affixed tab positioned so that the mask can be gripped with a single hand.

The mask of the present invention may include various features to facilitate gripping. In one embodiment, the mask 20 includes at least one tab 40 disposed on the outside surface 24, as depicted in FIGS. 3 and 5. The tab 40 extends outwardly from the outside surface 24 and is adapted to be gripped by the wearer for dispensing and donning. The tab 40 may be integral (FIG. 3) to the outside surface 24, i.e., it may be formed contemporaneously with the mask 20, so that the tab 40 is merely an extension of the outside surface 24 rather than a separate component affixed to the mask 20 during manufacturing or otherwise. As shown in FIG. 5, the tab 40 may alternatively be a separate component that is affixed to the outside surface 24 of the mask 20. In such embodiments, the tab 40 may be affixed to the outside surface 24 by stitching, thermal bonding, adhesive bonding, or by any other appropriate means. As used herein, the term "adhesive" refers to the property of any material that allows the material to bond together substrates by surface attachment.

The tab 40 may be located at any point on the outside surface 24 of the mask 20. In some embodiments, the tab 40 may be positioned in a substantially central region 42 on the outside surface 24. Such a point is generally distal to each point along the periphery 26. In this configuration, the tab 40 is positioned so that when the tab 40 is grasped, the mass of the mask 20 is substantially balanced in the wearer's hand, thereby stabilizing the mask 20 for donning.

The tab may be formed from any suitable material, such as an elastic material (e.g. a polymer), inelastic material, a nonwoven, knit, ribbon, cloth, wire, and so forth. As used herein, the term "elastic" refers to the ability of a material to recover its size and shape after deformation. As used herein, the term "inelastic" refers to the inability of a material to recover its size and shape after deformation. In some embodiments, the tab is formed from the same material selected to form the outside surface of the mask. The tab may, where desired, be substantially impervious to fluids. Alternately, the tab may be impervious to liquids. In some embodiments, the tab is formed from a filtration material such as those described below.

The tab is generally sized to allow gripping with two or more fingers of a single hand. The tab may have any shape, including rectangular, circular, oval, trapezoidal, star, flared, tapered, or otherwise. In some embodiments, the tab 40 has a projected area of at least about 10 mm$^2$ (0.0001 m$^2$). As used herein, the term "projected area" refers to the area of the tab that would project onto the outside surface of the mask. In other embodiments, the tab 40 may have a projected area of at least about 20 mm$^2$ (0.002 m$^2$).

The tab 40 generally extends outwardly from the outside surface 24 a sufficient distance Z1 so that the wearer of the mask 20 may grip the tab 40 between two or more fingers of a single hand. In some embodiments, the tab 40 may extend outwardly from the outside surface 24 at least 5 mm (0.005 m). In other embodiments, the tab 40 may extend outwardly from the outside surface 24 at least about 8 mm (0.008 m). In yet other embodiments, the tab 40 may extend outwardly at least about 10 mm (0.01 m) from the outside surface. In some embodiments, the tab 40 may extend outwardly from the surface a maximum distance of about 25 mm (0.025 m).

The tab may be tailored to suit the gripping characteristics of particular types of wearers. In some embodiments, the tab may be substantially rigid, so that a wearer can grip the tab without causing it to collapse. In other embodiments, the tab may be substantially deformable so that a wearer is able to compress the tab between two or more fingers when gripping it.

Figure 6:
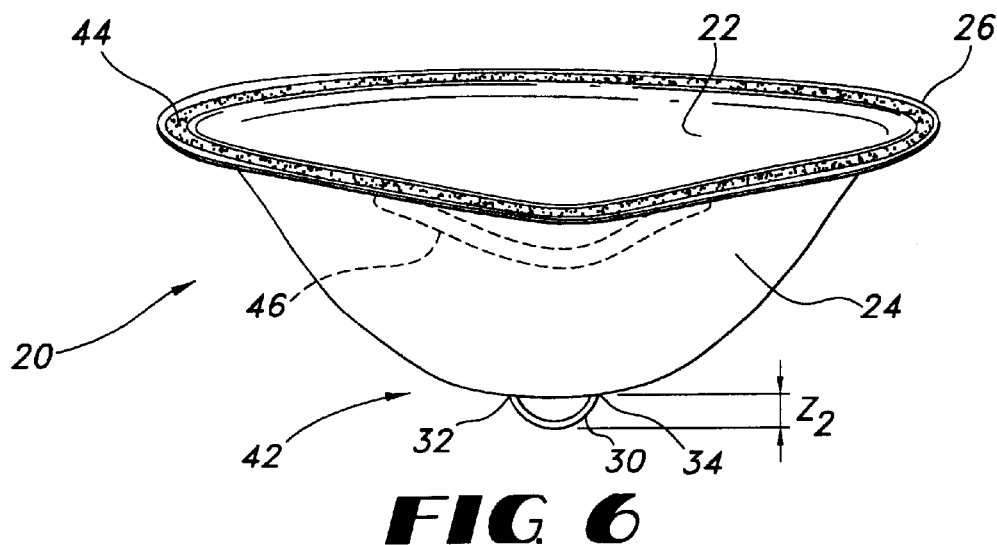
FIG. 6 is a perspective view of a cup shaped face mask having a flared edge periphery and a loop positioned so that the mask can be gripped with a single hand.

In another embodiment shown in FIG. 6, the mask 20 of the present invention may include at least one loop 30 having a first end 32 and a second end 34 attached to the outside surface 24. The loop 30 may be located at any point on the outside surface 24 of the mask 20. In some embodiments, the loop 30 may be positioned in a substantially central region 42 on the outside surface 24. Such a point is generally distal to each point along the periphery 26. In this configuration, the loop 30 is positioned so that when the loop 30 is gripped, the mass of the mask 20 is substantially balanced in the wearer's hand, thereby stabilizing the mask 20 for donning.

The loop may be formed from any suitable material, such as an elastic material (e.g. a polymer), inelastic material, a nonwoven, knit, ribbon, cloth, wire, and so forth. As used herein, the term "elastic" refers to the ability of a material to recover its size and shape after deformation. As used herein, the term "inelastic" refers to the inability of a material to recover its size and shape after deformation. In some embodiments, the loop is formed from the same material selected to form the outside surface of the mask. The loop may be bonded or otherwise affixed to the outside surface. Examples of suitable techniques include adhesive bonding, thermal bonding, stitching, and so forth. As used herein, the term "adhesive" refers to the property of any material that allows the material to bond together substrates by surface attachment.

The loop 30 is generally sized and positioned to facilitate gripping by a wearer, both prior to, during, and after donning. The loop 30 may be less than about 80 mm (0.08 m) in length as measured from the first end 32 to the second end 34 along the length of the loop 30. In other embodiments, the loop 30 may be less than about 60 mm (0.06 m) in length. In yet other embodiments, the loop 30 may be less than about 40 mm (0.04 m) in length. Where, in some embodiments, the loop is formed from an elastic material, the loop may have a fully extended length of 200 mm (0.200 m).

The loop 30 generally extends outwardly from the outside surface 24 a sufficient distance Z2 (FIG. 6) so that the wearer of the mask 20 may grip the loop 30 between two or more fingers of a single hand. In some embodiments, the loop 30 may extend outwardly from the outside surface 24 at least 5 mm 0.005 m). In other embodiments, the loop 30 may extend outwardly from the outside surface 24 at least about 8 mm (0.008 m). In yet other embodiments, the loop 30 may extend outwardly from the outside surface 24 at least about 10 mm (0.01 m) from the outside surface.

Figure 7:
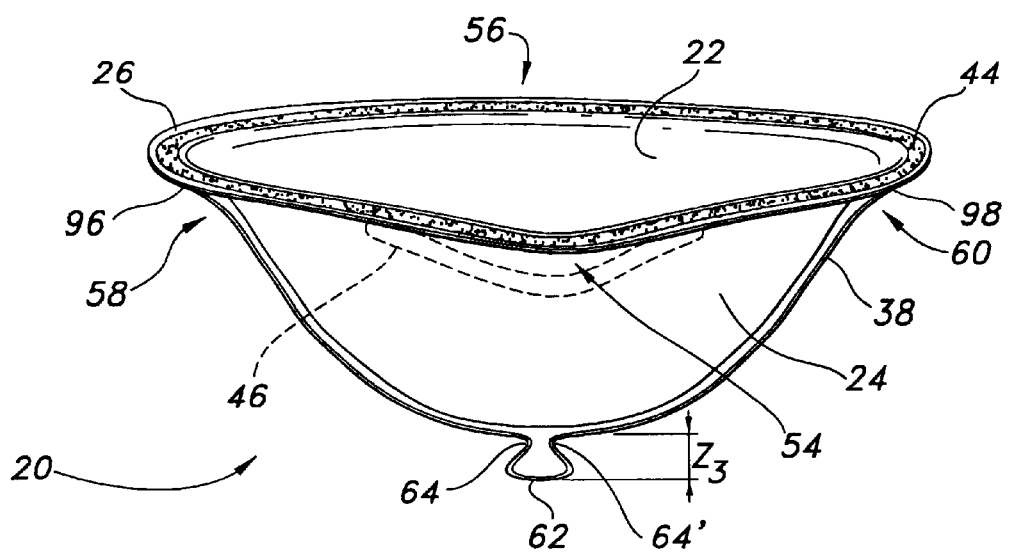
FIG. 7 is a perspective view of a cup shaped face mask having a loop with a fold positioned so that the mask can be gripped with a single hand.
Figure 8:
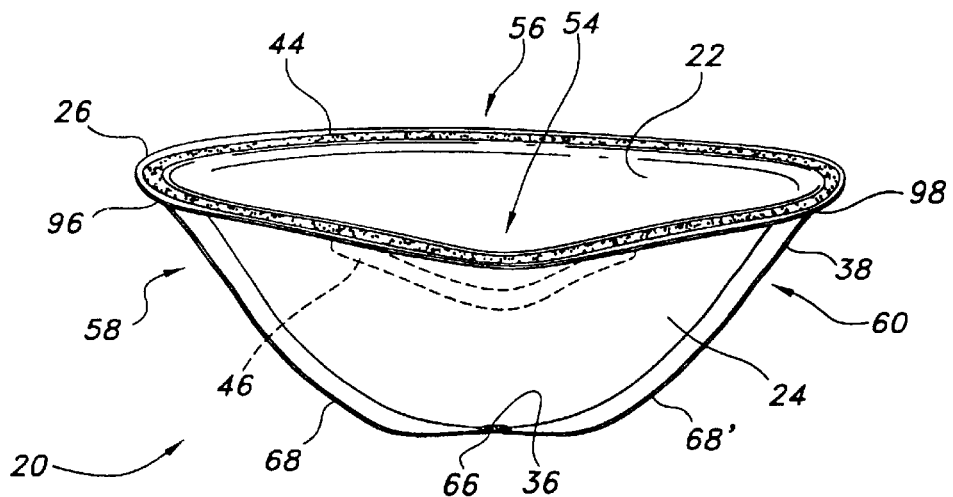
FIG. 8 is a perspective view of a cup shaped face mask having a loop with an intermediate point attached to the outside surface so that the mask can be gripped with a single hand.

In other embodiments depicted in FIGS. 7 and 8, the face mask of the present invention includes an outside surface 24 having an upper edge 54, a lower edge 56, a first side edge 58, and a second side edge 60. The upper edge 54 generally defines a region of the mask 20 that when donned follows the contours of the human face over the nose and along the upper portion of the cheeks to either side. The lower edge 56 generally defines a region of the mask 20 that when donned follows the contours of the human face along the chin and lower portion of the cheeks to either side. The first side edge 58 and second side edge 60 generally define the regions of the mask 20 that when donned extend from the nose portion to the chin portion along the cheek portions on both sides. It should be understood, however, that each edge as defined is contiguous to its respective adjacent edges so that all of the edges combined form a single border around the circumference or perimeter of the mask.

The mask 20 further includes a loop 38 having a first end 32 and a second end 34. The first end 32 and the second end 34 are attached to the outside surface 24 so that the loop 38 extends from the first side edge 58 to the second side edge 60. In some embodiments, the loop 38 may span the entire width of the outside surface 24 from the first side edge 58 to the second side edge 60 and may be substantially horizontal when donned. In some embodiments, the loop 38 may be disposed substantially equidistant from the upper edge 54 and the lower edge 56.

The loop may be formed from any suitable material, such as an elastic material (e.g. a polymer), inelastic material, a nonwoven, knit, ribbon, cloth, wire, and so forth. In some embodiments, the loop is formed from the same material selected to form the outside surface of the mask. The loop may be bonded or otherwise affixed to the outside surface. Examples of suitable techniques include adhesive bonding, thermal bonding, stitching, and so forth.

In some embodiments, the loop may also be used as a securing means. In such embodiments, the loop is extended around the back of the wearer's head, thereby securing the mask to the face of the wearer.

In one embodiment depicted in FIG. 7, the loop 38 may include a fold 62 disposed between the first end 32 and the second end 34 to facilitate gripping. The fold 62 in the loop 38 enables the wearer to grip the mask more easily, thereby facilitating donning and removal of the mask 20. The fold 62 may be located at any point along the length of the loop 38. In some embodiments, the fold 62 is disposed substantially equidistant from the first end 32 and the second end 34. In such an embodiment, the mass of the mask is substantially balanced to stabilize the mask in the hand of the wearer during donning.

The fold 62 in the loop 38 is generally sized and positioned to facilitate gripping by a wearer, both prior to and after donning. The fold 62 generally includes at least two creases 64 and 64' in the loop so that the fold 62 extends outward in a direction Z3 from the outside surface 24. The fold 62 may be less than about 30 mm (0.03 m) in length as measured between the two most distal crease in the loop. In other embodiments, the fold 62 may be less than about 20 mm (0.02 m) in length. In yet other embodiments, the fold 62 may be less than about 15 mm (0.015 m) in length.

The fold 62 generally extends outwardly from the outside surface 24 a sufficient distance Z3 so that the wearer of the mask 20 may grip the fold between two or more fingers of a single hand. In some embodiments, the fold 62 may extend outwardly from the outside surface 24 at least about 10 mm (0.01 m). In other embodiments, the fold 62 may extend outwardly from the outside surface 24 at least about 8 mm (0.008 m). In yet other embodiments, the fold 62 may extend outwardly from the outside surface 24 at least about 5 mm (0.005 m).

The creases 64 and 64' may be formed by any suitable technique, including thermal setting, thermal bonding, adhesive bonding or stiffening, wires, chemical additives, and so forth. The loop may be formed from a material to enhance crease formation and gripping, and in some embodiments, may be flat and wide or ribbon-like.

In another embodiment illustrated in FIG. 8, to facilitate gripping, the loop 38 may include an intermediate point 66 disposed between the first end 32 and the second end 34. The intermediate point 66 may be affixed to the outside surface 24 between the first side edge 58 and the second side edge 60. The intermediate point 66 divides the loop 38 into two segments 68 and 68' that may be gripped individually or simultaneously by the wearer to facilitate donning of the mask 20. In some embodiments, the intermediate point 66 may be substantially equidistant from the first end 32 and the second end 34, thereby substantially balancing the mass of the mask 20 in the wearer's hand. The intermediate point 66 may be removably affixed to the outside surface 24. In some embodiments, the intermediate point 66 may be removably affixed to the outside surface 24 by a bead 36 of an adhesive material. Such an adhesive material used for this purpose may have a sufficiently low adhesion strength so that when the loop is detached from the adhesive material, mask is not damaged and the efficacy of the mask is retained.

Figure 9:
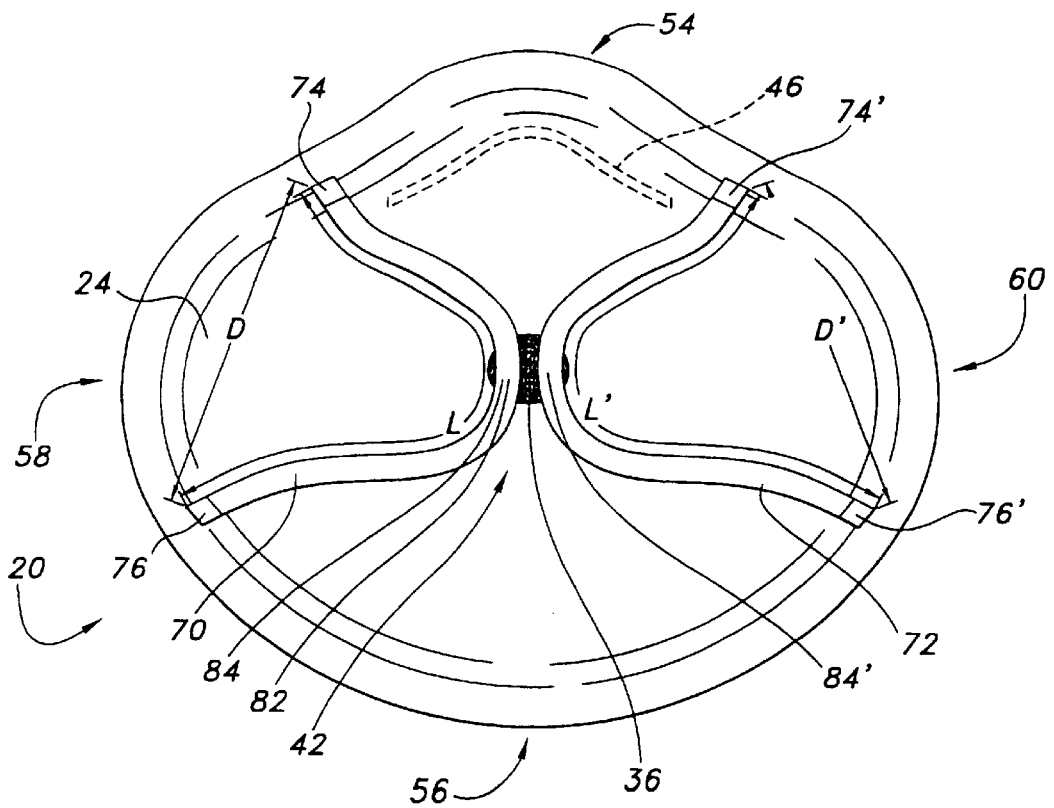
FIG. 9 is a top plan view of a cup shaped face mask having a first loop and a second loop attached to the mask, each loop having an intermediate point removably affixed to the outside surface.
Figure 10:
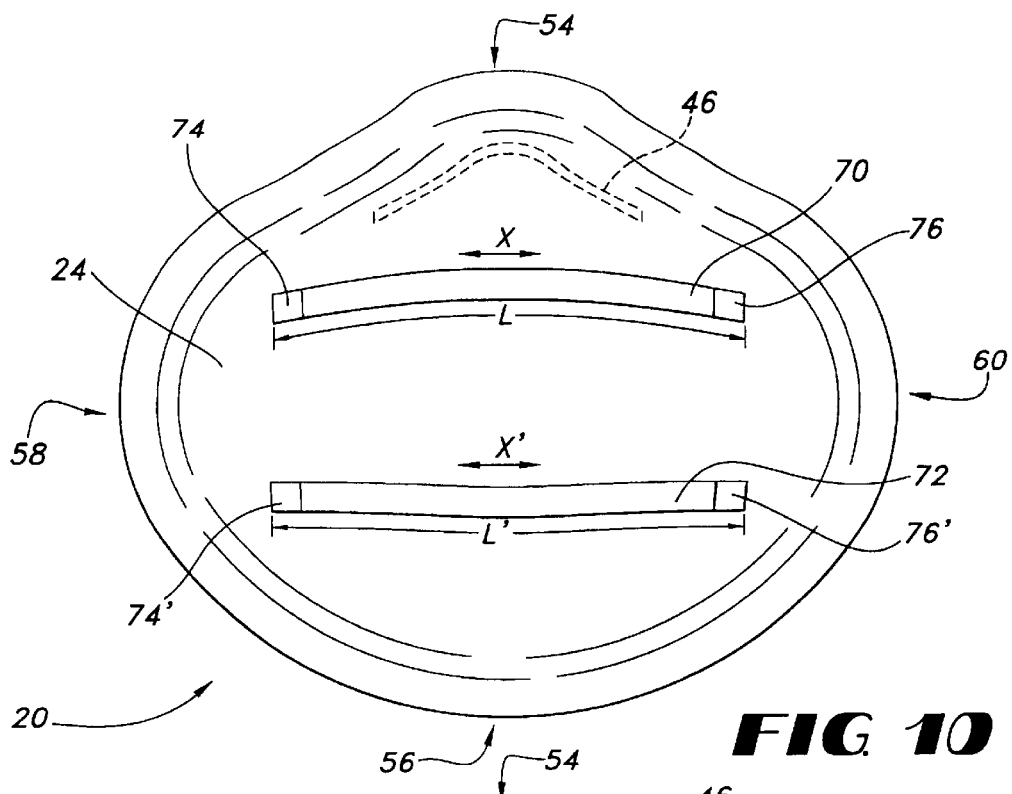
FIG. 10 is a top plan view of a cup shaped face mask having a first loop and a second loop, each extending from a first side edge to a second side edge of the outside surface and spaced so that the first loop and the second loop can be gripped with a single hand.
Figure 11:
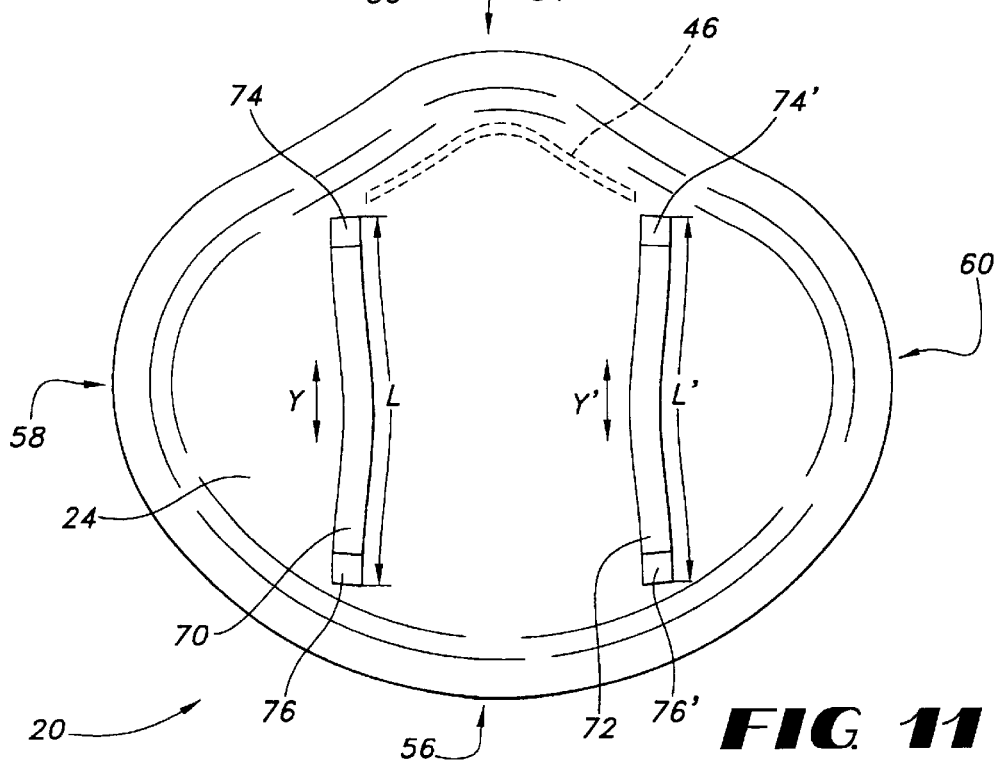
FIG. 11 is a top plan view of a cup shaped face mask having a first loop and a second loop, each extending from an upper edge to a lower edge of the outside surface and spaced so that the first loop and the second loop can be gripped with a single hand.

FIGS. 9, 10, 11 depict other masks made according to the present invention. Such masks include at least a first loop 70 and a second loop 72 disposed on the outside surface 24. The first loop 70 and the second loop 72 are spaced so that a wearer can grip the first loop 70 and the second loop 72 with a single hand. Each loop 70 and 72 includes a first end 74 and 74', a second end 76 and 76', and a length L and L' measured between the first end 74 and 74' and the second end 76 and 76'.

The first loop and the second loop may be formed from any suitable material, such as an elastic material (e.g. a polymer), inelastic material, a nonwoven, knit, ribbon, cloth, wire, and so forth. In some embodiments, the loop is formed from the same material selected to form the outside surface of the mask. The loop may be bonded or otherwise affixed to the outside surface. Examples of suitable techniques include adhesive bonding, thermal bonding, stitching, and so forth. Further, the first loop and the second loop may be configured in a variety of manners, including those described below.

In one embodiment depicted in FIG. 9, the first end 74 and the second end 76 of first loop 70 are attached proximal to the first side edge 58. The length L of the first loop 70 may be sufficient in magnitude, so that, when attached to the outside surface 24, the length L is greater than the attachment distance D. As used herein, "attachment distance" means the distance between the first end and second end of the loop as measured directly on the outside surface of the mask. Where the length L is greater than the attachment distance D, the unattached portion of the loop 70 may tend to lie flat on the outside surface 24 of the mask 20, forming a curvilinear shape. Such shape may be parabolic, and in some instances, the vertex 82 of the parabola lies near the central region 42 of the outside surface 24. Where the second loop 72 likewise has a length L' greater than its attachment distance D', the first loop 70 may oppose the second loop 72 in a symmetrical curvilinear relation on the outside surface 24.

In some embodiments, the first loop 70 may include an first intermediate point 84 between the first end 74 and the second end 76. The first intermediate point 84 may be affixed to the outside surface 24. In some embodiments, the second loop 72 may include a second intermediate point 84' between the first end 74' and the second end 76'. The second intermediate point 84' may be affixed to the outside surface 24. The first intermediate point 84 may be substantially equidistant from the first end 74 and the second end 76 of the first loop 70 and may form the vertex 82 of the parabolic shape described above. Likewise, the second intermediate point 84' may be substantially equidistant from the first end 74' and the second end 76' of the second loop 72. In some embodiments, the first intermediate point 84 and/or the second intermediate point 84' are removably affixed to the outside surface 24.

Various means of removably affixing the first intermediate point 84 and the second intermediate point 84' may be used, including for example, a bead 36 of an adhesive material, an adhesive tape (not shown), and so forth. In some embodiments, the first loop and the second loop may be used as ear loops to secure the mask to the face of the wearer (not shown). In such an embodiment, after the mask is gripped and brought into contact with the face of the wearer the wearer may detach the intermediate points from the outside surface and don the ear loops.

In another embodiment depicted in FIG. 10, the first end 74 and the second end 76 of the first loop 70 are attached proximal to the upper edge 54 and the first end 74' and the second end 76' of the second loop 72 are attached proximal to the lower edge 56, such that the first loop 70 and the second loop 72 extend in a direction X and X' from the first side edge 58 to the second side edge 60. Alternatively, in another embodiment depicted in FIG. 11, the first end 74 and the second end 76 of the first loop 70 are attached proximal to the first side edge 58 and the first end 74' and the second end 76' of the second loop 72 are attached proximal to the second side edge 60, such that the first loop 70 and the second loop 72 extend in a direction Y and Y' from the upper edge 54 to the lower edge 56. The first loop and second loop are spaced so that a wearer can grip the first loop and the second loop to facilitate donning. The first loop may be parallel to the second loop on the outside surface. Other loop configurations are contemplated by the present invention, including additional loops, overlapping loops, and so forth.

The above-described features are designed to enable the wearer to grasp the mask with a single hand, usually between the thumb and one or more fingers. The wearer is then able to bring the mask into contact with his or her face so that the periphery is positioned in a comfortable location. In some embodiments, an adhesive material 44 may be applied to the periphery 26 (FIGS. 3, 5–8) to enhance comfort, fit, efficacy, and so forth. In such embodiments, the mask may be donned with a single hand, thereby providing a significant advantage over many commercially available masks that require use of two hands to properly position the mask on the wearer's face and secure the mask to the wearer's face. Any adhesive material used must be suitable for application to the skin.

Certain polysiloxane adhesives are believed suitable for use with the present invention. One such adhesive material is described in U.S. Pat. No. 5,618,281 to Betrabet et al., incorporated herein by reference in its entirety. Other suitable adhesive materials include those described in U.S. Pat. No. 5,658,270 to Lichstein, incorporated herein by reference in its entirety. However, it is contemplated that other suitable pressure-sensitive adhesive materials known in the art may be used with the present invention.

Alternatively, a temperature-sensitive adhesive material that is substantially nontacky at or below about 25° C. that becomes tacky upon contact with skin may be used. As used herein, the term "substantially nontacky" refers to a substance that exhibits a tack of less than about 5 g/cm² of force as measured by ASTM D2979. As used herein, the term "tacky" refers to a substance that exhibits a tack of at least about 10 g/cm² of force as measured by ASTM D2979. In this test, the tack value is expressed as grams of force required to remove the end of a stainless steel rod 5.0 mm in diameter from the surface of an adhesive material coating at a speed of 10 mm per second to which it has been adhered for 1.0 second. Suitable adhesive materials have a narrow melting transition range to ensure a rapid change from a substantially nontacky state to a tacky state. By way of example only, suitable temperature-sensitive adhesive materials are provided by U.S. Pat. No. 5,156,911 to Stewart, incorporated herein by reference in its entirety. However, it is contemplated that other suitable temperature-sensitive adhesive materials known to those of skill in the art may be used with the present invention.

The face mask may also incorporate any combination of known features, such as visors or shields, beard covers, etc. (not shown). Ear loops may also be attached to the mask proximal to the periphery so that if the medical personnel is required to remain in the sterile environment for an extended period of time, the worker is able to don the ear loops to further secure the mask to the face (not shown). The mask 20 may also include an elongated malleable member 46 (FIGS. 1, 3, 5–14) disposed proximal to at least a portion of the periphery 26 for configuring the mask 20 to closely fit the contours of the nose and cheeks of the wearer. The malleable member 46 may be made of any malleable material including, but not limited to, metal wire or an aluminum band.

The face mask of the present invention may be formed from a variety of materials and fabrics, such as woven reusable fabrics and nonwoven disposable fabrics or webs. As used herein, the term "nonwoven fabric" or "nonwoven web" or "nonwoven material" means a web having a structure of individual fibers or threads that are randomly interlaid, but not in an identifiable manner or pattern as in a knitted fabric. Nonwoven fabrics or webs have been formed from many processes, for example, meltblowing processes, spunbonding processes, and bonded carded web processes.

As used herein, the term "spunbond" or "spunbond fibers" or "spunbonded fibers" refers to small diameter fibers that are formed by extruding molten thermoplastic material as filaments from a plurality of fine, usually circular capillaries of a spinneret with the diameter of the extruded filaments then being rapidly reduced, for example, as in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al.

As used herein, the term "meltblown" or "meltblown fibers" means fibers formed by extruding a molten thermoplastic material through a plurality of fine, usually circular, die capillaries as molten threads or filaments into converging high velocity, usually hot, gas (e.g. air) streams that attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al.

The face mask may be formed from a single layer of material or a composite of multiple layers. In the case of multiple layers, the layers are generally positioned in a juxtaposed or surface-to-surface relationship and all or a portion of the layers may be bound to adjacent layers. The multiple layers of a composite may be joined to form a multilayer laminate by various methods, including but not limited to adhesive bonding, thermal bonding, or ultrasonic bonding. One composite material suitable for use with the present invention is a spunbond/meltblown/spunbond (SMS) laminate. An SMS laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Multilayer laminates may have multiple meltblown layers or multiple spunbond layers in many different configurations and may include materials other than nonwovens. Examples of such other materials include wovens, films, foam/film laminates and combinations thereof, for example, a spunbond/film/spunbond (SFS) laminate. Examples of other composite materials suitable for use in the present invention include, but are not limited to, those described in U.S. Pat. No. 4,041,203 to Brock et al., U.S. Pat. No. 5,169,706 to Collier, et al., U.S. Pat. No. 5,145,727 to Potts et al., U.S. Pat. No. 5,178,931 to Perkins et al., U.S. Pat. No. 4,374,888 to Bornslaeqer, and U.S. Pat. No. 5,188,885 to Timmons et al., which are all incorporated herein by reference.

The face mask of the present invention may include a layer of material, for example, a nonwoven material, suitable for filtration. The filtration material may be made from a meltblown nonwoven web and, in some embodiments, may be subject to electret treating. As used herein, the term "electret" or "electret treating" refers to a treatment that imparts a charge to a dielectric material, such as a polyolefin. The charge includes layers of positive or negative charges trapped at or near the surface of the polymer, or charge clouds stored in the bulk of the polymer. The charge also includes polarization charges that are frozen in alignment of the dipoles of the molecules. Methods of subjecting a material to electret treating are well known by those skilled in the art. These methods include, for example, thermal, liquid-contact, electron beam, and corona discharge methods. One particular technique of subjecting a material to electret treating is disclosed in U.S. Pat. No. 5,401,466, the contents of which are herein incorporated in its entirety by reference. This technique involves subjecting a material to a pair of electrical fields wherein the electrical fields have opposite polarities. Electret treatment results in a charge being applied to the filtration medium that further increases filtration efficiency by drawing particles to be filtered toward the filter by virtue of their electrical charge. Electret treatment can be carried out by a number of different techniques. One technique is described in U.S. Pat. No. 5,401,446 to Tsai et al. assigned to the University of Tennessee Research Corporation and incorporated herein by reference in its entirety. Other methods of electret treatment are known in the art, such as that described in U.S. Pat. No. 4,215,682 to Kubik et al., U.S. Pat. No. 4,375,718 to Wadsworth, U.S. Pat. No. 4,592,815 to Nakao and U.S. Pat. No. 4,874,659 to Ando, incorporated herein by reference in their entirety.

Alternatively, the mask may include a layer of expanded polytetrafluoroethylene (PTFE) membrane for filtration, such as those manufactured by W. L. Gore & Associates. A more complete description of the construction and operation of such materials can be found in U.S. Pat. No. 3,953,566 to Gore and U.S. Pat. No. 4,187,390 to Gore, incorporated herein by reference in their entirety.

The minimum filtration efficiency requirements differ for various applications. The filtration efficiency of the face mask may be expressed in terms of its sodium chloride (NaCl) efficiency. The NaCl efficiency measures the ability of a fabric or web to prevent the passage of small particles (about 0.1 micron) through it. A higher efficiency is generally more desirable and indicates a greater ability to remove particles. The NaCl efficiency may be measured by an automated filter tester. One such apparatus is available from TSI, Inc., P.O. Box 64394, 500 Cardigan Rd, St. Paul, Minn. 55164, designated as the Model 8110 Automated Filter Tester (AFT). The Model 8110 AFT measures pressure differential and particle filtration characteristics for air filtration media. The AFT utilizes a compressed air nebulizer to generate a submicron aerosol of sodium chloride particles that serve as the challenge aerosol for measuring filter performance. The characteristic size of the particles used in these measurements is 0.1 micron. Typical air flow rates are between 31 liters per minute and 33 liters per minute. The AFT test is performed on a sample area of about 140 cm$^2$. The performance or efficiency of a filter medium is expressed as the percentage of sodium chloride particles that penetrate the filter, penetration being defined as transmission of a particle through the filter medium. The transmitted particles are detected downstream from the filter using a light scattering technique. The percent penetration (% P) reflects the ratio of the downstream particle count to the upstream particle count. In some embodiments, the mask may have a NaCl efficiency above 80 percent. In some other embodiments, the mask may have a higher filtration efficiency, for example, from about 95 percent to about 99.997 percent. In some embodiments, the maximum pressure differential through the mask may be less than 5 millimeters of water (mm H2O).

Where present, the filtration layer may also be required to attain a desired bacterial filtration efficiency (BFE). The BFE is a measure of the ability of a material to prevent the passage of bacteria through it. Face masks for medical applications may require a BFE of greater than or equal to about 96%. BFE may be measured according to military specification MIL-M-36954C, 4.4.1.1.1 and 4.4.1.2. The BFE is expressed as a percentage with a maximum efficiency of 100%. The BFE of a material may be measured, for instance, by Nelson Laboratories of Salt Lake City, Utah.

Figure 12:
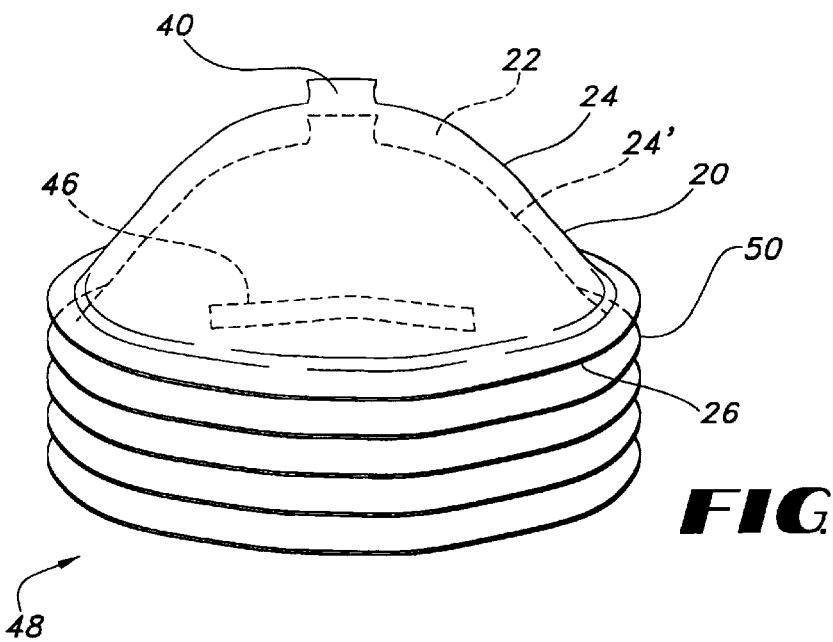
FIG. 12 is a side plan view of a plurality of face masks shown in FIG. 5 placed in a stacked configuration.
Figure 13:
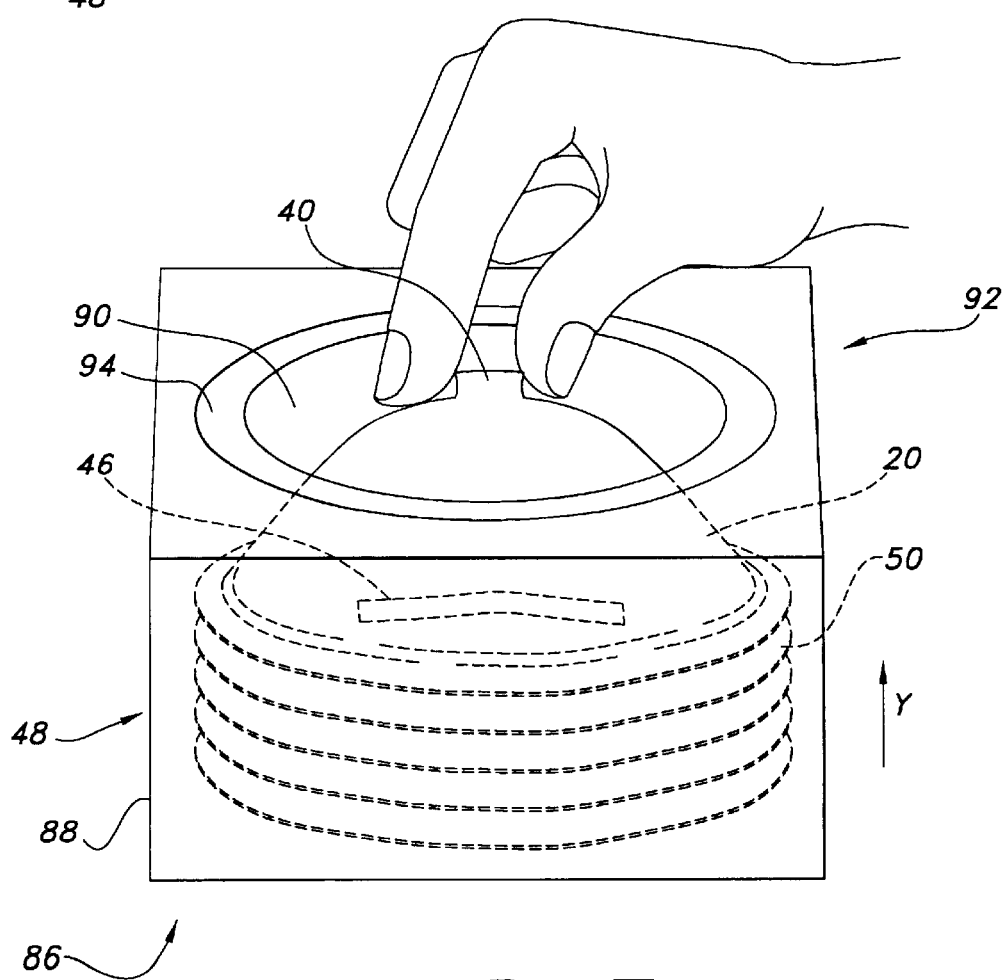
FIG. 13 is a perspective view of an exemplary dispenser for dispensing the face mask of the present invention, dispensing the mask depicted in FIG. 5.
Figure 14:
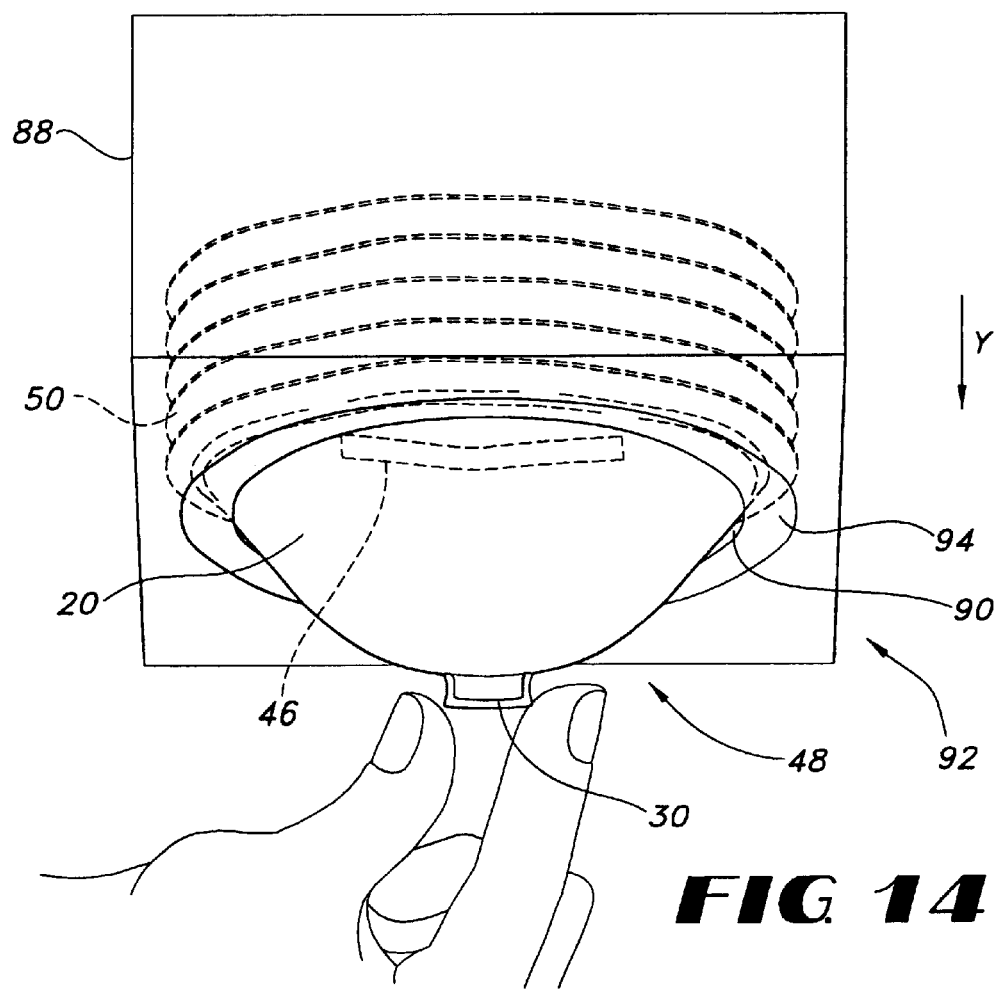
FIG. 14 is a perspective view of an exemplary dispenser for dispensing the face mask of the present invention, dispensing the mask depicted in FIG. 6.

The present invention also contemplates positioning a plurality of masks described above in a stacked configuration as depicted in FIG. 12. The masks 20 and 50, for example, are positioned in a nestled relation to one another with the inside surface 22 of one mask 20 being apposed to the outside surface 24' of another mask 50. As used herein, the term "apposed" refers to a juxtaposed or proximal relation. The masks are adapted so that, when placed in a stacked configuration, a distance is maintained between masks.

In some embodiments, the shape of the mask is adapted to maintain the distance between apposed masks. By way of example only, the outside surface may include a tab integral with and extending outwardly from the outside surface (as shown in FIG. 12), wherein the tab is adapted for gripping. Such a tab may extend outwardly at least 5 millimeters from the outside surface, thereby creating a distance D3 between apposed masks 20 and 50 so that the periphery 26 of one mask 20 does not contact the outside surface 24' of an adjacent mask 50.

In other embodiments, outside surface of the mask is adapted to maintain the distance between apposed masks. By way of example only, in one embodiment, the outside surface includes a loop having a first end and a second end, each attached to the outside surface, the loop having a length of less than about 80 millimeters. In another embodiment, the outside surface includes a top edge, bottom edge, a first side edge, and a second side edge, and a loop having a first end attached proximal to the first side edge, a second end attached proximal to the second side edge, and a fold in the loop disposed between the first end and the second end. Such features create and maintain a distance between apposed masks so that the periphery of one mask does not contact the outside surface of an adjacent mask. In some embodiments, a distance of at least 3 mm (0.003 m) may be maintained. In other embodiments, a distance of at least about 5 mm (0.005 m) may be maintained. In yet other embodiments, a distance of at least about 8 mm (0.008 m) may be maintained. In still other embodiments, a distance of at least about 10 mm (0.01 m) may be maintained.

As stated above, some mask embodiments may include an adhesive material on at least a portion of the periphery. Due to the presence of the tab, loop, or any other gripping feature described herein on the outside surface and the distance maintained thereby, such masks may be placed in a stacked configuration without having the adhesive material contact the outside surface of the apposed mask. Thus, in some embodiments, there may not be a need for a release paper to be used in conjunction with the adhesive material. Thus, the wearer may easily remove a mask from the stack and don it with a single hand.

The present invention also includes an apparatus for dispensing a mask, such as the masks described above. However, it is contemplated that the dispenser of the present invention may be used with other mask configurations not described herein. The dispenser 86 (FIGS. 13 and 14) generally includes a plurality of walls 88 and an opening 90 (best seen in FIG. 13). The dispenser 86 may include mounting screws or other fastening means (not shown) to affix the dispenser to a rigid surface (not shown). For instance, the fastening means may be used to affix the dispenser to a wall, table, or the like (not shown).

The opening 90 may bear any relation to the mounting surface, and in some embodiments, the opening 90 is disposed in the dispenser 86 so that it may be affixed to the rigid surface. The masks 20 and 50 may advance in a direction Y toward the opening 90 by means of gravity or otherwise, or may alternatively dispense in any other direction (not shown), provided that some means is provided to bias the mask 20 toward the opening 88. Such means may include a spring device, such as that described in U.S. Pat. No. 5,012,952 to Franz, incorporated herein by reference in its entirety.

The dispenser 86 of the present invention may be configured to dispense a mask 20 from a stack 48 of substantially identical nested cup shaped masks 20. The masks 20 include a flanged periphery 26 and are placed in the dispenser 86. The masks 20 may be biased toward a dispensing end 92 of the of the dispenser 86 by any suitable means, including gravity, spring mechanisms, or the like, so that dispensing a mask causes the stack to advance toward the opening. The dispenser 86 includes a flexible support element, or diaphragm 94, disposed astride the dispensing end 92 and in engagement with the flanged periphery 26 of the mask 20. The diaphragm 94 secures the mask 20 from dislodgment from the housing when the mask 20 is not being dispensed, but is yieldable so that the mask 20 may displace the diaphragm 94 and be removed during dispensing. The diaphragm 94 may be formed from any suitable material, including a flexible polymeric material or the like.

The present invention also includes a method of dispensing a face mask, such as the masks described above, to facilitate one-handed gripping and donning. The method of the present invention may be used with any mask configuration. However, the use of the dispenser of the present invention in conjunction with the method and mask of the present invention further facilitates dispensing and donning, as will be described below.

The method of dispensing of the present invention includes providing a shaped face mask comprising an inside surface and an outside surface, the outside surface adapted to be gripped with a single hand. The mask is positioned in a nestled relation to another mask, the inside surface of the mask apposed to the outside surface of an adjacent mask, thereby forming a stack having an outermost mask.

A dispenser is provided for storage of the stack and dispensing of the outermost mask. In general, any dispenser shape or size may be used with the present invention. The dispenser includes a plurality of walls and a dispensing end, and the dispensing end includes a resilient diaphragm having an opening. The resilient diaphragm may be formed from any material, provided that it is sufficiently strong to support at least the partial weight of a complete stack of masks, for example, when the dispenser has just been filled, and sufficiently flexible so that when the mask is being removed from the dispenser, the mask is able to overcome the diaphragm and be removed. Various polymers may be suitable for use with the present invention, including for example, polypropylene, polyethylene, natural rubber, and so forth.

The stack is placed in the dispenser so that at least a portion of the outermost mask may be gripped through the opening. To do so, at least a portion of the outside surface of the mask may extend through the opening. In other embodiments, the outside surface of the mask does not extend through the opening, but the opening is sufficiently sized so that a wearer can reach through the opening to grasp the mask. In either configuration, the outermost mask may be removed through the opening, the resilient diaphragm retaining the remainder of the stack in the housing. Upon removal of the outermost mask, the mask apposed to the dispensed mask advances toward the opening and becomes the outermost mask.

Various masks may be used with the method of the present invention to facilitate dispensing and donning of the mask, provided that the outside surface of the mask is adapted to be gripped with a single hand. In one embodiment, the outside surface includes a tab disposed on and extending outwardly from the outside surface, wherein the tab is adapted for gripping. In another embodiment, the outside surface includes a loop having a first end and a second end, each attached to the outside surface, the loop having a length of less than about 80 millimeters. In yet another embodiment, the outside surface includes a top edge, bottom edge, a first side edge, and a second side edge, and the outside surface includes a loop having a first end attached to the outside surface proximal to the first side edge, a second end attached to the outside surface proximal to the second side edge, and a fold in the loop disposed between the first end and the second end.

In summary, the combination of the above-described mask and dispensing features enables the wearer to grasp the mask from the dispenser with a single hand and bring the mask into contact with his or her face, thereby presenting a substantial benefit over typical masks that require two hands for donning. This system offers greater versatility and efficiency by enabling the wearer to use his or her available hand for transporting equipment, supplies, or the like.

The invention may be embodied in other specific forms without departing from the scope and spirit of the inventive characteristics thereof. The present embodiments therefore are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of dispensing a face mask comprising:
   providing a shaped face mask comprising an inside surface and an outside surface, the outside surface comprising a tab disposed on and extending outwardly from the outside surface adapted to be gripped with a single hand;
   positioning the mask in a nestled relation to another mask, the inside surface of the mask apposed to the outside surface of an adjacent mask, thereby forming a stack having an outermost mask;
   providing a dispenser for storage of the stack and dispensing of the outermost mask, the housing having a plurality of walls and a dispensing end, the dispensing end including a resilient diaphragm having an opening;
   placing the stack in the dispenser such that at least a portion of the outermost mask may be gripped through the opening; and
   removing the outermost mask through the opening, the resilient diaphragm retaining the remainder of the stack in the housing, such that the mask apposed to the dispensed mask becomes the outermost mask.

2. The method of claim 1, the outside surface comprising a loop having a first end and a second end, each attached to the outside surface, the loop having a length of less than about 80 millimeters.

3. The method of claim 1, the outside surface having a top edge, bottom edge, a first side edge, and a second side edge, the outside surface comprising a loop having a first end attached to the outside surface proximal to the first side edge, a second end attached to the outside surface proximal to the second side edge, and a told in the loop disposed between the first end and the second end.

4. The method of claim 1, wherein the mask is cup shaped.

5. A system for dispensing a mask comprising:
   a dispenser having a stack of a plurality of shaped masks contained therein, the dispenser having an opening toward which the stack is biased and a flexible support element disposed astride the opening adapted to secure the stack from dislodgment while being sufficiently yieldable to allow the mask to overcome the flexible support element and be removed from the dispenser;
   the mask comprising an outside surface adapted to be gripped through the opening, the outside surface comprising a tab disposed on and extending outwardly from the outside surface, wherein the tab is adapted for gripping.

6. The dispenser of claim 5, wherein dispensing the mask causes the stack to advance toward the opening.

7. A stack of face masks comprising:
   a plurality of shaped face masks having an inside surface and an outside surface, the outside surface comprising a tab integral with and extending outwardly from the outside surface, wherein the tab is adapted for gripping, the inside surface having a periphery with an adhesive material disposed on at least a portion thereof, the masks being positioned in a nestled relation to one another, the inside surface of the mask being apposed to the outside surface of an adjacent mask, thereby forming a stack,
   wherein the shape of the masks is adapted to maintain a distance between apposed masks so that the periphery of a mask does not contact the outside surface of an apposed mask.

8. The stack of claim 7, the tab extending outwardly at least 5 millimeters from the outside surface.

9. The stack of claim 7, wherein the shape of the outside surface of the mask is adapted to maintain the distance between apposed masks.

10. The stack of claim 9, the outside surface comprising a loop having a first end and a second end, each attached to the outside surface, the loop having a length of less than about 80 millimeters.

11. The stack of claim 9, the outside surface having a top edge, bottom edge, a first side edge, and a second side edge, the outside surface comprising a loop having a first end attached proximal to the first side edge, a second end attached proximal to the second side edge, and a fold in the loop disposed between the first end and the second end.

12. The stack of claim 11, the fold extending outwardly from the outside surface at least 5 millimeters.

13. The stack of claim 7, wherein the distance between apposed masks is at least 3 millimeters.

14. The stack of claim 7, wherein the distance between apposed masks is at least about 5 millimeters.

15. The stack of claim 7, wherein the distance between apposed masks is about 8 millimeters.

16. The stack of claim 9, wherein the distance between apposed masks is at least about 10 millimeters.

17. A stack of face masks comprising:
   a plurality of shaped face masks having art inside surface and an outside surface, the inside surface having a periphery with an adhesive material disposed on at least a portion thereof, the masks being positioned in a nestled relation to one another, the inside surface of the mask being apposed to the outside surface of an adjacent mask, thereby forming a stack, the outside surface having a top edge, bottom edge, a first side edge, and a second side edge, the outside surface comprising a loop having a first end attached proximal to the first side edge, a second end attached proximal to the second side edge, and an intermediate point between the first end and the second end, the intermediate point being affixed to the outside surface between the first side edge and the second side edge, wherein the shape of the outside surface of the masks is adapted to maintain a distance between apposed masks so that the periphery of a mask does not contact the outside surface of an apposed mask.

18. A stack of face masks comprising:

a plurality of shaped face masks having an inside surface and an outside surface, the inside surface having a periphery with an adhesive material disposed on at least a portion thereof, the masks being positioned in a nestled relation to one another, the inside surface of the mask being apposed to the outside surface of an adjacent mask, thereby forming a stack, the outside surface having a top edge, bottom edge, a first side edge, and a second side edge, the outside surface comprising a first loop and a second loop, each having a first end, a second end, and a length measured between the first end and the second end, the first loop and the second loop attached to the outside surface such that a wearer can grasp the first loop and the second loop with a single hand, wherein the shape of the outside surface of the masks is adapted to maintain a distance between apposed masks so that the periphery of a mask does not contact the outside surface of an apposed mask.

19. The stack of claim 18, the first loop being attached proximal to the first side edge, the first end and the second end of the first loop having a first loop attachment distance, and the second loop being attached to proximal to the second side edge, the first end and the second end of the second loop having a second loop attachment distance, wherein the first loop has a length greater than the first loop attachment distance, and the second loop has a length greater than the second loop attachment distance, such that when the mask is not donned, the first loop opposes the second loop in a curvilinear relation on the outside surface.

20. The stack of claim 19, the first loop having an first intermediate point between the first end and the second end, and the second loop having a second intermediate point between the first end and the second end, wherein the first intermediate point and the second intermediate point are removably affixed to the outside surface.

21. The stack of claim 18, wherein the first end and the second end of the first loop are attached proximal to the upper edge and the first end and the second end of the second loop are attached proximal to the lower edge, such that the first loop and the second loop extend in a direction from the first side edge to the second side edge.

22. The stack of claim 18, wherein the first end and the second end of the first loop are attached proximal to the first side edge and the first end and the second end of the second loop are attached proximal to the second side edge, such that the first loop and the second loop extend in a direction from the upper edge to the lower edge.

* * * * *